United States Patent [19]

Bauer et al.

[11] Patent Number: 5,670,705
[45] Date of Patent: Sep. 23, 1997

[54] *GERBERA JAMESONII* PLANTS HAVING INCURVING MATURE RAY FLORETS

[75] Inventors: Eric Geoffrey Bauer; Constance Adelaide Bauer, both of Queensland, Australia

[73] Assignee: Flor Igene Pty Ltd., Collingwood Vic, Australia

[21] Appl. No.: 493,179

[22] Filed: Jun. 21, 1995

Related U.S. Application Data

[63] Continuation of Ser. No. 181,355, Jan. 13, 1994, abandoned, which is a continuation of Ser. No. 579,165, Sep. 6, 1990, abandoned.

[51] Int. Cl.$^6$ .................................................. A01H 5/00
[52] U.S. Cl. ............................... 800/200; Plt./68.1; 47/58; 47/DIG. 1; 435/172.2
[58] Field of Search .................................. 800/200, 205; 47/58; 435/172.2; Plt./68.1

[56] References Cited

U.S. PATENT DOCUMENTS

| P.P. 7,244 | 6/1990 | Segers | Plt./68.1 |
| P.P. 7,318 | 9/1990 | Segers | Plt./68.1 |

*Primary Examiner*—Gary Benzion
*Attorney, Agent, or Firm*—Townsend and Townsend and Crew LLP

[57] ABSTRACT

New and distinguishable strains of *Gerbera jamesonii* characterized by the presence in flowers thereof of full incurring of both ray and outer disc florets.

9 Claims, 3 Drawing Sheets

GERBERA JAMESONII PLANTS HAVING INCURVING MATURE RAY FLORETS

CROSS REFERENCE TO RELATED APPLICATIONS

This application is a continuation of U.S. application Ser. No. 08/181,355 filed Jan. 13, 1994, which is a continuation of application Ser. No. 07/579,165, filed Sep. 6, 1990, both now abandoned.

BACKGROUND OF THE INVENTION

The present invention relates to the development of new strains of Gerbera known as *Bauerii Bundabergia*. The new strains grow on strong straight stems and set multiple large incurving rows of brightly colored florets. Additionally, the mentioned characteristics are stable through regeneration of the plants.

The Gerbera species is a native of Africa and a close relative of the daisy family. The original Botanical classification was done by Jameson who named several colored varieties *Gerbera jamesonii*. The common names are: Daisy or Barberton daisy or Transvaal daisy.

The native Gerberas are small standing weakly stemmed plants bearing 7.5 cm diameter flowers of cream, deep pink, yellows and oranges with only a single row of ray florets. The color traits of the native flowers are highly variable and unstable through regeneration.

The inventors of the present invention started a concentrated effort of twenty years duration to improve the appearance and utility of the original native *Gerbera jamesonii* (Barberton daisy). Using similar techniques to those described herein a variety known as Nobleflora and sub varieties were developed. These varieties, unlike the native Gerberas, grow large multi floretted flowers with flat or slightly reflexing petals. The flower is supported on a fasciated stem of five to fifteen millimeters in diameter. Wide variations in color have been developed as sub varieties. The sub varieties have been exported to many countries and are available as both seed and cell culture from commercial nurseries.

The new strains with the desired characteristics were obtained by a systematic breeding program. Using two commercially available varieties: *Gerbera jamesonii* Var Nobleflora subvar Royal Lady as the mother plant and *Gerbera jamesonii* Var Nobleflora subvar Venture as the male donor, a recurrent selective breeding program, over ten years duration, was established. The outcome of which are the new strains of Gerbera hereinafter sometimes referred to as Bauerin Bundabergia, having the same combination of morphological traits described herein.

SUMMARY OF THE INVENTION

According to the present invention there is provided new and distinguishable strains of Gerbera plants characterized by the following morphological traits; conspicuously saccate nature of the leaf blade; bilobed (in transection) petuncle which is 2–3 times as wide as that in the native Gerbera species; proliferation of rows of involucral bracts to at least 8 from 5 in the native Gerbera species; in the proliferation of ray florets from one in the native Gerbera species to many in the new strains; in the cohesion of the teeth at the tip of outer lips of the ray florets and also in the disc florets causing the tips to be hooded and curled inwards and in the case of the disc florets causing the tips of the inner lips to be held in the hooded tip of the outer lips.

The new strains can be reproduced by seed, division of stools, and by cloning via tissue culture (micropropagation). Asexual and sexual reproduction of the new strains has shown that the herein described and other distinguishing characteristics come true to form and are established and transmitted through succeeding propagations.

DESCRIPTION OF THE PREFERRED EMBODIMENTS

Figure 1:
FIG. 1 One of the parent strains *Gerbera jamesonii* Var Nobleflora subvar Royal Lady.

In one particularly preferred embodiment there is provided a new cultivar which is described in the following botanical description:

Acaulescent herbs. Leaves basal, alternate, petiolate, elliptic or oblanceolate in outline, irregularly and deeply lobed especially at the base, sparsely pilose on both surfaces, conspicuously saccate between the main veins;

Peduncles densely pilose, approximately 10 mm in diameter at its widest point, bilaterally symmetrical in transection with two partly fused channels running length of the peduncle tissue, the channels hollow or partly filled with soft tissue;

Heads approximately 10 cm in diameter, the involucre approximately 4 cm in diameter, with densely pilose involucral bracts in 6–8 rows;

Ray florets female, fertile, in many rows, either all similar or with the inner ray florets much smaller and similar in size and color to the disc florets, staminodes present corollar bilabiate:

in outer ray florets the outer lip 3.0–4.5 cm long, 4–5 times longer than the tube, with 3 teeth usually cohering into a hooded tip, the inner lip ½ to ⅓ that length, of two filiform coiled lobes; in inner ray florets (where present) the outer lip about 5 mm long, twice as long as the tube with 3 teeth usually cohering into a hooded tip, the inner tip, the inner lip of two filiformcoilcd lobes as long as the outer lip;

Disc florets bisexual, fertile, in many rows; corolla about 10 mm long, bilabiate or unilabiate, the lips equal in length; outer lip oblong with 3–6 teeth often cohering into a hooded tip; inner lip of 2–3 linear lobes enclosed at the tip by the hooded outer lip or reflexed, or absent. Anthers linear, tailed, with a lanceolate appendage;

Ovary of all florets oblong, fibbed, glandularpilose, slightly beaked; pappus of many bristles 6–8 mm long, united in a ring at the base or fused in bundles.

In yet further embodiments there are provided numerous color variations however all plants share the same distinguishing morphological traits as described above.

The following colors are given in color values and terminology in accordance with The Royal Horticultural Society Color Chart 1966, Royal Horticultural Society, London and were recorded from corollas of florets from eight heads of the plant:

| Top surface: | Red 46B striped with 46A & 53A |
|---|---|
| Under surface: | Red 47A & 47B |
| Top: | Red 53A & 47A tipped with Yellow 11C & 11D |
| Under: | Yellow 11C & 11D |
| Top: | Red 49A striped with 49D |
| Under: | Red 49D |
| Top: | Red 51A stripped with 52B |
| Under: | Red 36D with Yellow 12D at base |
| Top: | Red 53A |
| Under: | Red 54A |
| Top: | Orange-red 34A striped with Yellow 8A |
| Under: | Yellow 8A striped with Orange-red 34A |
| Top: | Orange-red 30C striped with Orange 25A |
| Under: | Orange 25C |
| Top: | Orange-red 33C & 32C |
| Under: | Yellow-orange 17D |

These strains differ from the parent species in the following ways:
In the conspicuously saccate nature of the leaf blade;
In the bilobed (in transection) peduncle which is 2 to 3 times as wide as that in the species;
In the proliferation of rows of involucral bracts to 8 from 5 in the species;
In the proliferation of my florets to many rows from one row in the species;
In the cohesion of the teeth at the tip of outer lips of the ray florets and often also in the disc florets, causing the tips to be hooded and curled inwards, and in the case of the disc florets causing the tips of the inner lips to be held inn the hooded tip of the outer lips;
In the complex coloring of the florets as described above.

Details of the Breeding Methodology with Reference to the Drawings STAGE (i)

Pollen from *Gerbera jamesonii* var Nobleflora subvar Venture was used to pollinate *Gerbera jamesonii* Var Noble flora subvar Royal Lady (FIG. 1), The progeny, which showed any incurring of both ray and outer disc florets, were saved for the next stage.

STAGE (ii)

Figure 2:
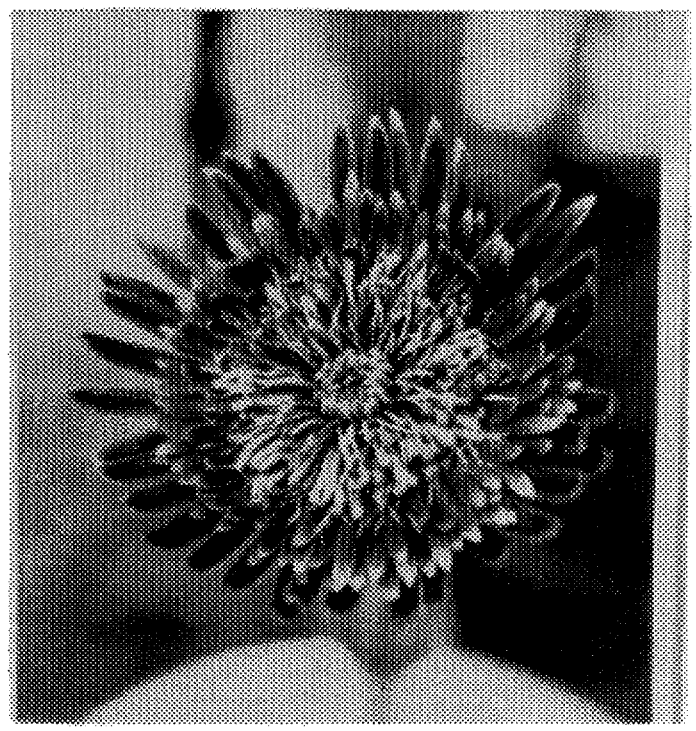
FIG. 2 First stage progeny used as stock for second stage pollen donors in a back cross to *Gerbera jamesonii* var Nobleflora subvar Royal Lady.

The progeny of Stage (i), i.e., those showing incurring (FIG. 2), were used as male donors in a back cross to Royal Lady. The progeny which possessed enhanced incurring of ray mad outer disc florets and further showed development of intermediate and central disc florets were saved for the next stage.

STAGE (iii)

Figure 3:
FIG. 3 Second stage progeny used as stock for third stage breeding program.

The progeny of Stage (ii), i.e., the progeny showing enhanced incurring and development of inner florets (FIG. 3), were self pollinated. Plants which had full incurring of ray and outer disc florets as well as fully developed intermediate and central florets were selected for the next stage of breeding.

STAGE (iv)

Figure 4:
FIG. 4 Third stage progeny used as stock for the fourth stage breeding program.
Figure 5:
FIG. 5 Fourth stage progeny illustrative of the invention and used as a stock for the fifth stage of the breeding program producing other varieties in accordance with the invention.

Those plants from Stage (iii) which showed the highest incurring and development of florets (approximately 10%) (FIG. 4) were allowed to interpollinate. The resulting progeny showed fully developed florets and full incurring characteristics (approximately 96% of progeny) (FIG. 5). A wide range of colors was also obtained.

STAGE (v)

Individual clones from Stage (iv) with the desired characteristics were self pollinated for four generations to check the stability of color and characteristics. No instability was observed.

Asexual reproduction of the new strains of Gerbera was achieved by well known horticultural methods.

These strains of Gerbera are most easily characterized by their large incurving flower heads growing on wide fasciated stems.

It is apparent from the foregoing that modifications and variations are possible within the spirit of the invention, Accordingly, the scope of the invention should be limited only by the appended claims.

We claim:

1. Strains of *Gerbera jamesonii* resulting from the crossing of *Gerbera jamesonii* varieties Nobleflora subvar 'Royal Lady' as the female parent and Nobleflora subvar 'Venture' as the male parent and all mutants, variants and derivatives thereof that produce mature ray florets having incurving such that the petal of the florets initially extend radially outwards from the center of the inflorescence and the distal ends of the petals then curve upwards and inwards towards the center of the inflorescence.

2. Strains of Gerbera according to claim 1 having the following combination of morphological traits: an inflorescence having full incurving of both ray and outer disc florets; conspicuously saccate leaf blade; bilobed, in transection, peduncle which is 2–3 times as wide as that in the native Gerbera species; at least 8 rows of involucral bracts; more than one row of ray florets; cohesion of the teeth at the tip of outer lips of the ray florets and also in the disc florets causing the tips to be hooded and curled inwards and, in the case of the disc florets, causing the tips of the inner lips to be held in the hooded tip of the outer lips.

3. Strains of Gerbera according to claim 1 also having the following combination of morphological traits:

Acaulescent herbs;

Leaves being basal, alternate, petiolate, elliptic or oblanceolate in outline, irregularly and deeply lobed especially at the base, sparsely pilose on both surfaces, conspicuously saccate between the main veins;

Peduncles being densely pilose, approximately 10 mm in diameter at the widest point, bilaterally symmetrical in transection with two partly fused channels running the length of the peduncle tissue, the channels hollow or partly filled with soft tissue;

Heads being approximately 10 cm in diameter, having an involucre approximately 4 cm in diameter, with densely pilose involucral bracts in 6–8 rows;

Disc florets being bisexual, fertile, in many rows; corolla about 10 mm long, bilabiate or unilabiate, the lips equal in length; outer lip oblong with 3–6 teeth often cohering into a hooded tip; inner lip of 2–3 linear lobes enclosed at the tip by the hooded outer lip or reflexed, or absent;

Ray florets being female, fertile, in many rows, either all similar or with inner ray florets being much smaller and similar in size and color to the disc florets, staminodes present, corolla bilabiate:

The ray florets having an outer lip 3.0–4.5 cm long, 4–5 times longer than the tube, with 3 teeth usually cohering into a hooded tip;

The inner ray florets, where present, having an outer lip about 5 mm long, twice as long as the tube with 3 teeth usually cohering into a hooded tip;

Anthers being linear, tailed, with a lanceolate appendage;

Ovaries of all florets oblong, ribbed, glandular-pilose, slightly beaked; and

A pappus of many bristles 6–8 mm long, united in a ring at the base or fused in bundles.

4. Propagating material from plants of the strains of Gerbera claimed in claim 1.

5. Flowers produced by plants of the strains of Gerbera claimed in claim 1.

6. A plant resulting from the clonal propagation of the plants of the strains of Gerbera claimed in claim 1.

7. A *Gerbera jamesonii* plant of claim 1 resulting from the sexual propagation of plants of said strains of *Gerbera jamesonii*.

8. A plant resulting from the asexual propagation of plants of the strains of Gerbera claimed in claim 1.

9. Seeds from plants of the strains of *Gerbera jamesonii*, wherein said seeds produce the *Gerbera jamesonii* claimed in claim 1.

* * * * *